United States Patent
Agresti et al.

(10) Patent No.: US 11,965,891 B2
(45) Date of Patent: *Apr. 23, 2024

(54) DIGITAL PROTEIN QUANTIFICATION

(71) Applicants: Bio-Rad Laboratories, Inc., Hercules, CA (US); Bio-Rad Europe Gmbh, Basel (CH)

(72) Inventors: Jeremy Agresti, Richmond, CA (US); Ronald Lebofsky, Kensington, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/393,445

(22) Filed: Dec. 29, 2016

(65) Prior Publication Data

US 2017/0192013 A1    Jul. 6, 2017

Related U.S. Application Data

(60) Provisional application No. 62/273,249, filed on Dec. 30, 2015.

(51) Int. Cl.
| | |
|---|---|
| *G01N 33/68* | (2006.01) |
| *B01J 19/00* | (2006.01) |
| *C12Q 1/68* | (2018.01) |
| *C12Q 1/6816* | (2018.01) |
| *C12Q 1/6869* | (2018.01) |
| *C40B 20/04* | (2006.01) |
| *C40B 70/00* | (2006.01) |

(52) U.S. Cl.
CPC ...... *G01N 33/6878* (2013.01); *B01J 19/0046* (2013.01); *C12Q 1/6816* (2013.01); *C12Q 1/6869* (2013.01); *C40B 20/04* (2013.01); *C40B 70/00* (2013.01)

(58) Field of Classification Search
CPC ...... B01J 19/0046; C40B 70/00; C40B 20/04; C12Q 1/6816; G01N 33/6878
See application file for complete search history.

(56) References Cited

U.S. PATENT DOCUMENTS

| | | | | |
|---|---|---|---|---|
| 8,383,061 B2 * | 2/2013 | Prakash | ............... | F16K 99/0001 422/502 |
| 2005/0037397 A1 | 2/2005 | Mirkin et al. | | |
| 2009/0118158 A1 * | 5/2009 | Quay | ................ | A61K 38/1709 514/1.1 |
| 2010/0173394 A1 | 7/2010 | Colston, Jr. et al. | | |
| 2012/0220494 A1 * | 8/2012 | Samuels | ............ | C12N 15/1075 506/16 |
| 2013/0143745 A1 | 6/2013 | Christen et al. | | |
| 2013/0323732 A1 * | 12/2013 | Anderson | .............. | B01D 15/08 435/6.12 |
| 2014/0099637 A1 * | 4/2014 | Nolan | .................. | C12Q 1/6813 435/325 |
| 2014/0357500 A1 * | 12/2014 | Vigneault | .......... | C12N 15/1037 506/4 |
| 2015/0018236 A1 | 1/2015 | Green et al. | | |
| 2015/0197790 A1 | 7/2015 | Tzonev | | |

FOREIGN PATENT DOCUMENTS

| | | | | |
|---|---|---|---|---|
| WO | WO-2012106385 A2 * | 8/2012 | .......... | C12Q 1/6806 |
| WO | 2014/065756 A1 | 5/2014 | | |
| WO | 2014/204939 A2 | 12/2014 | | |
| WO | WO-2014194131 A2 * | 12/2014 | .......... | C12Q 1/6874 |
| WO | WO-2015103339 A1 * | 7/2015 | ....... | C12Q 2525/191 |
| WO | 2015/200893 A2 | 12/2015 | | |
| WO | WO-2015200893 A2 * | 12/2015 | ......... | C12N 15/1065 |

OTHER PUBLICATIONS

Kuhlmann ("Fixation of biological specimens." (2009)) (Year: 2009).*
International Search Report and Written Opinion from Application No. PCT/US2016/069129, dated Mar. 17, 2017.
Stoeckius, et al., "Large-scale simultaneous measurement of epitopes and transcriptomes in single cells", bioRxiv preprint, Mar. 2, 2017, Retrieved from the Internet at URL: http://dx.doi.org/10.1101/113068.
Extended European Search Report for EP Application No. 16882646.9 dated Apr. 23, 2019; 9 pages.
Gong, H. et al.; "Simple Method to Prepare Oligonucleotide-Conjugated Antibodies and Its Application in Multiplex Protein Detection in Single Cells"; Bioconjugate Chemistry; vol. 27, No. 1; Dec. 21, 2015; pp. 217-225.
Head, S.R. et al.; "Library construction for next-generation sequencing: Overviews and challenges"; *Biotechniques Rapid Dispatches*; vol. 56, No. 2; Feb. 1, 2014; pp. 61-77.

* cited by examiner

*Primary Examiner* — Sahana S Kaup
(74) *Attorney, Agent, or Firm* — Withers Bergman, LLP; Thomas C. Meyers

(57) ABSTRACT

Methods and compositions are described for single cell resolution, quantitative proteomic analysis using high throughput sequencing.

9 Claims, 1 Drawing Sheet

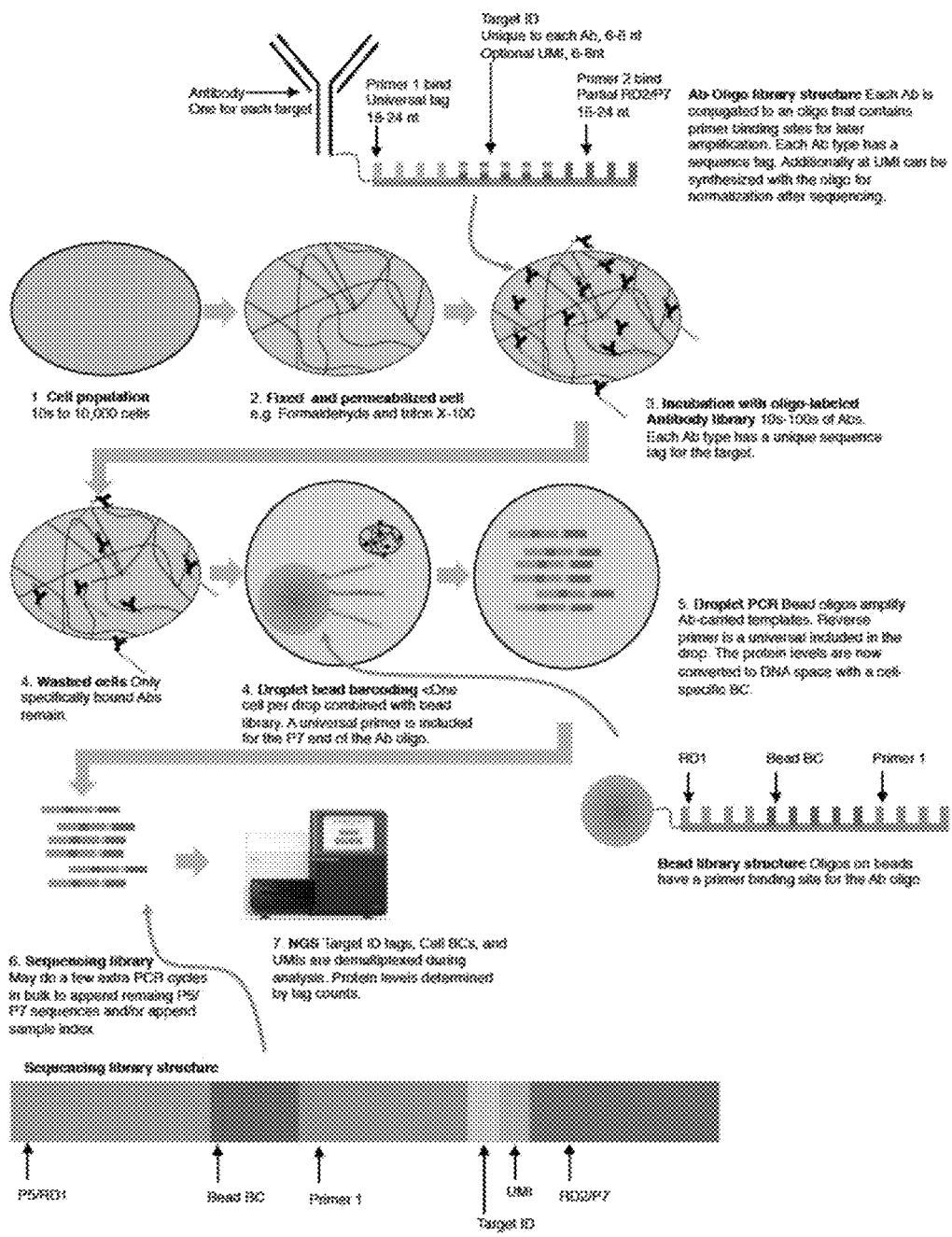

DIGITAL PROTEIN QUANTIFICATION

CROSS-REFERENCES TO RELATED APPLICATIONS

This application claims priority to U.S. Provisional Application No. 62/273,249, filed on Dec. 30, 2015, the contents of which are hereby incorporated by reference in the entirety for any and all purposes.

BACKGROUND OF THE INVENTION

Next generation sequencing methods have enabled quantitative analysis of thousands of nucleic acid markers at the level of entire organisms down to single cells. By contrast, quantitative analysis of other biological components such as proteins has proven much more difficult. Methods such as FACS, ELISA, and bead-based multiplexing are limited by lack of sensitivity, sample throughput, and the number of markers that can be analyzed simultaneously. Methods such as mass cytometry require expensive and specialized heavy atom labeling to work and have been limited to a few tens of simultaneous markers for all but the most sophisticated of users.

BRIEF SUMMARY OF THE INVENTION

Described herein are methods and compositions for quantitative analysis of biological components such as proteins at the single cell level. The analysis is performed by encoding level of the biological components of a single cell into oligonucleotide barcode sequences. The methods and compositions involve the production and use of libraries of binding elements (e.g., antibodies or aptamers), where each binding element is tagged with an identifiable oligonucleotide barcode. The binding elements specifically bind different target ligands (e.g., proteins, antigens, etc.). The binding elements can be contacted with a set of target ligands of a single cell to form binding-element:ligand complexes. The levels of the binding-element ligand complexes can be detected by recovering and sequencing the oligonucleotide barcodes bound to the binding elements. The analysis can be performed in a highly parallel fashion in which 10's to 10,000's or more single cells are analyzed simultaneously.

In one aspect, the present invention provides a plurality of mixture partitions, wherein the individual mixture partitions comprise: i) a plurality of fixed proteins, wherein all of the fixed proteins in the individual mixture partition are from one cell; and ii) a library of at least about 10 structurally distinct antibodies, wherein the structurally distinct antibodies have a specific binding affinity for, and are bound to, structurally distinct target epitopes of the fixed proteins, and wherein the structurally distinct antibodies are conjugated to target-epitope specific oligonucleotides with an optionally cleavable linker, wherein the target-epitope specific oligonucleotides comprise: a) target-epitope specific barcode sequences, wherein the target-epitope specific barcode sequences are the same for any one structurally distinct antibody and different for all other structurally distinct antibodies; and b) optionally, unique molecular identifier sequences, wherein the optional unique molecular identifier sequences are different for every molecule of target-epitope specific oligonucleotide.

In another aspect, the present invention provides a plurality of mixture partitions, wherein the individual mixture partitions comprise: i) a plurality of fixed proteins, wherein all of the fixed proteins in the individual mixture partition are from one cell; ii) a library of at least about 10 structurally distinct antibodies, wherein the structurally distinct antibodies have a specific binding affinity for, and are bound to, structurally distinct target epitopes of the fixed proteins; iii) a plurality of double-stranded target-epitope specific oligonucleotides, wherein the individual double-stranded target-epitope specific oligonucleotides are either covalently linked to a corresponding individual structurally distinct antibody, cleaved from the corresponding individual structurally distinct antibody, or comprise a reverse complement of an oligonucleotide covalently linked to or cleaved from the corresponding individual structurally distinct antibody, and wherein the target specific oligonucleotides comprise: a) target-epitope specific barcode sequences, wherein the target-epitope specific barcode sequences are the same for any one structurally distinct antibody and different for all other structurally distinct antibodies; b) optional unique molecular identifier sequences, wherein the unique molecular identifier sequences are different for every target-epitope specific oligonucleotide; c) a partition-specific barcode sequence that is identical among all partition-specific oligonucleotides of any one mixture partition and different from all partition-specific barcode sequences in other mixture partitions of the plurality of mixture partitions; d) a first 5' region comprising a first sequencing primer binding region; and e) a second 5' region comprising a second sequencing primer binding region, wherein the first and second primer binding regions are on opposite strands of the double stranded target-epitope specific oligonucleotide, are structurally different from each other, and flank the target-epitope specific barcode sequence, partition-specific barcode sequence, and optional universal molecular identifier sequence.

In another aspect, the present invention provides a high throughput sequencing library comprising a plurality of double stranded polynucleotides, wherein the library represents a level, of a plurality of target epitopes of a single cell, wherein the individual double-stranded polynucleotides comprise: i) a single-cell specific barcode sequence, wherein the single-cell specific barcode sequence is the same for all double-stranded polynucleotides; ii) an epitope target identifier sequence, wherein the epitope target identifier sequence is unique for every structurally distinct target epitope; and iii) an optional universal molecular identifier sequence, wherein the universal molecular identifier sequence is unique to every double-stranded polynucleotide of the library, wherein the double-stranded polynucleotides comprise high throughput sequencing adaptors flanking i), ii), and, if present, iii).

In another aspect, the present invention provides any one of the foregoing pluralities of high throughput sequencing libraries, wherein each library encodes a level, of a plurality of target epitopes of a unique single cell.

In another aspect, the present invention provides a method for generating the plurality of mixture partitions of claim 3, the method comprising: i) providing a fixed and permeabilized plurality of single cells, wherein individual fixed and permeabilized single cells comprise the fixed proteins of one single cell; ii) incubating the fixed and permeabilized plurality of single cells with the library of at least about 10 structurally distinct antibodies conjugated to the target-epitope specific oligonucleotides, thereby binding the antibodies to their corresponding epitopes, if present, to form a plurality of antibody library—single-cell epitope complexes; iii) washing away unbound antibodies; iv) partitioning the plurality of antibody library—single-cell complexes into the plurality of mixture partitions, and optionally discarding mixture partitions that do not contain a single cell and/or contain multiple cells; and v) partitioning a plurality of partition-specific barcode oligonucleotides into the plurality of partitions, and optionally discarding mixture partitions that do not contain a single partition-specific barcode sequence and/or contain multiple partition-specific barcode sequences.

In a first aspect, the present invention provides a partition containing a particle comprising a solid support surface, the solid support surface having a plurality of oligonucleotide primers conjugated thereon, wherein the plurality of oligonucleotide primers comprise: a 3' end that is available for ligation and/or extension by a polymerase; a 5' end that is linked to the solid support surface; and at least one barcode region. In some embodiments, the at least one barcode region comprises a partition-specific barcode, wherein the partition-specific barcode is substantially the same in the plurality of oligonucleotide primers conjugated to the solid support surface. In some embodiments, the at least one barcode region comprises a molecular barcode, wherein the molecular barcode of each of the plurality of oligonucleotides conjugated to the solid support surface is substantially unique.

In some embodiments, the at least one barcode region comprises a particle barcode and a molecular barcode. In some embodiments, the plurality of oligonucleotide primers comprise: a first defined region comprising a defined sequence of 10-100 nucleotides; a particle barcode comprising 6-20 nucleotides, wherein all, substantially all, or a majority of the plurality of oligonucleotide primers comprise the same particle barcode; and a molecular barcode comprising 6-20 nucleotides, wherein all, or substantially all, of the plurality of oligonucleotide primers comprise a unique molecular barcode. In some embodiments, the first defined sequence comprises a 3' capture region. In some embodiments, the capture region comprises a randomer, a poly-thymine, or a poly-adenosine sequence.

In some embodiments, the plurality of oligonucleotide primers conjugated to the solid support surface each comprise a hairpin region. In some embodiments, the hairpin region comprises a uracil. In some embodiments, the plurality of oligonucleotide primers each comprise a uracil at the 5' end of the oligonucleotide. In some embodiments, the plurality of oligonucleotide primers are conjugated to the solid support surface via a disulfide linkage. In some embodiments, the oligonucleotide primers comprise a double stranded region along at least a portion of the 3' end of the primers. In some embodiments, the plurality of oligonucleotide primers are double stranded. In some embodiments, the double stranded oligonucleotides or the portions of the oligonucleotides that are double stranded comprise a passivated 5' end. In some embodiments, the passivated 5' end comprises a 5' hydroxyl group (OH). In some embodiments, the partition comprises a droplet. In some embodiments, the partition can contain at least 10; 100; 200; 300; 500; 750; 1000; 2500; 5000; 7,500; 10,000; 15,000; 20,000; 30,000; 50,000; 100,000; $1 \times 10^6$; $1 \times 10^7$; or more copies of the partition-specific barcode, wherein the copies are identical or substantially identical, and unique or substantially unique as compared to partition-specific barcodes in other partitions, if present.

In a second aspect, the present invention provides a plurality of any one of the foregoing partitions, wherein the plurality of partitions comprises at least about 1,000; 10,000; 50,000; 100,000; 500,000; 1,000,000 or more particles comprising unique particle barcodes, wherein the unique particle barcodes are substantially the same for each particle and substantially unique between particles. In some embodiments, the partitions comprise, on average, 1 or fewer particles per partition. In some embodiments, the partitions comprise oligonucleotides cleaved from, on average, one or fewer barcoded particles. In some embodiments, the plurality of partitions comprise target nucleic acid. In some embodiments, the plurality of partitions comprise, on average, target nucleic acid of 1 or fewer cells per partition. In some embodiments, the target nucleic acid is mRNA and the particles comprise a poly-thymine capture region. In some embodiments, the target nucleic acid is cDNA and the particles comprise a poly-adenosine or poly-thymine capture region. In some embodiments, the partitions comprise droplets.

In another aspect, the present invention provides a method for performing single-cell resolution target epitope analysis by high throughput sequencing, the method comprising: i) forming or providing any one of the foregoing pluralities of mixture partitions, wherein the mixture partitions further comprise a thermostable polymerase, and wherein: a) the target-epitope specific oligonucleotides are covalently conjugated to the structurally distinct antibodies with a cleavable linker; b) the partition-specific oligonucleotides are covalently conjugated to the beads with a cleavable linker; or c) a) and b); and ii) cleaving the cleavable linkers of a), b), or c); iii) firstly hybridizing: a) the 3' priming regions of the partition-specific oligonucleotides to 5' ends of the target-epitope specific oligonucleotides, and extending the hybridized partition specific oligonucleotides with the polymerase, thereby generating double stranded target-epitope specific oligonucleotides comprising the target-epitope specific barcode sequences, the partition-specific barcode sequences, and optionally universal molecular identifier sequences; or b) the 3' priming regions of the universal primers to 5' ends of the target-epitope specific oligonucleotides, and extending the hybridized universal primers with the polymerase, thereby generating double stranded target-epitope specific oligonucleotides comprising a universal priming region, the target-epitope specific barcode sequences, and optionally universal molecular identifier sequences; and iv) secondly hybridizing: a) the 3' priming regions of the partition-specific oligonucleotides to 5' ends of the double-stranded target-epitope specific oligonucleotides comprising the universal priming regions, if present, and extending the hybridized partition specific oligonucleotides with the polymerase; or b) the 3' priming regions of the universal primers to 5' ends of the double-stranded target-epitope specific oligonucleotides comprising the partition-specific barcode sequences, if present, and extending the hybridized universal primers with the polymerase, thereby generating double stranded target-epitope specific oligonucleotides comprising the universal priming region, the target-epitope specific barcode sequences, the partition-specific barcode sequences, and optionally universal molecular identifier sequences; and v) amplifying the double stranded target-epitope specific oligonucleotides of iv); and vi) combining and sequencing the amplified double stranded target-epitope specific oligonucleotides in a high throughput sequencing reaction to obtain a number of target-epitope specific oligonucleotide sequence reads, wherein the sequencing comprises: a) determining the partition-specific barcode sequence, thereby determining the single cell to which the sequencing data corresponds; and b) determining the target-epitope specific barcode sequence, thereby determining the protein epitope to which the sequencing data corresponds, wherein the number of target-epitope specific oligonucleotide sequence reads, in which the reads have the same partition-specific barcode sequence and target-epitope specific barcode sequence is proportional to a level of the epitope in the single cell to which the sequencing data corresponds.

BRIEF DESCRIPTION OF THE DRAWINGS

FIG. 1: illustrates an embodiment of a method for high-throughput single cell quantitative proteomics. In this embodiment, the binding elements are antibodies directed to protein targets. The antibodies are conjugated to oligonucleotides containing a target ID barcode, primer binding sites, and optionally a universal molecular identifier. A population of 10's to 10,000 cells (1) are fixed and permeabilized (2), and contacted with a library of such antibody-oligonucleotide conjugates to form antibody:ligand complexes, and unbound antibodies are washed away (3). The single cells are partitioned into a plurality of droplets, to form a plurality of droplets that each contain a single cell, a polymerase, a universal primer and a bead, where the bead is conjugated to a plurality of oligonucleotides having a droplet-specific barcode and a primer region (4). The oligonucleotides conjugated to the beads and/or the oligonucleotides conjugated to the antibodies are cleaved. The antibody oligonucleotides are amplified with the polymerase universal primer and bead oligonucleotides, converting target protein levels into countable sequence tags (5). The droplets are combined to generate a sequencing library (6), which is sequenced using next generation (high-throughput) sequencing methodologies, converting sequence tag counts to target protein levels (7).

DEFINITIONS

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4$^{th}$ ed. 2007); Sambrook et al., MOLECULAR CLONING, A LABORATORY MANUAL, Cold Spring Harbor Lab Press (Cold Spring Harbor, NY 1989). The term "a" or "an" is intended to mean "one or more." The term "comprise," and variations thereof such as "comprises" and "comprising," when preceding the recitation of a step or an element, are intended to mean that the addition of further steps or elements is optional and not excluded. Any methods, devices and materials similar or equivalent to those described herein can be used in the practice of this invention. The following definitions are provided to facilitate understanding of certain terms used frequently herein and are not meant to limit the scope of the present disclosure.

As used herein, the term "complement" or "complementary" in reference to a primer, barcode, adaptor, or oligonucleotide sequence or region can include the reverse complement or reverse complementarity as required to maintain functionality of the primer, barcode, adaptor, or oligonucleotide. For example, where a single-stranded oligonucleotide contains one or more barcode sequences flanked by two different primer binding sequences for PCR amplification, one of skill in the art will understand that one of the two primer binding sequences of the single-stranded oligonucleotide is a reverse complement of the sequence of one primer, and the other is the same as a sequence of the other primer, or a portion thereof. Binding of the hybridizing portion of one primer to its reverse complement and extension by polymerization generates the binding site for the hybridizing portion of the second primer.

The term "binding element" refers to a molecule (e.g., a protein, nucleic acid, aptamer, etc.) that specifically interacts with or specifically binds to a target biological component (e.g., a target protein, antigen, oligonucleotide, carbohydrate, small molecule, etc.). Non-limiting examples of molecules that specifically interact with or specifically bind to a target biological component include nucleic acids (e.g., oligonucleotides), proteins (e.g., antibodies or binding fragments thereof, transcription factors, zinc finger proteins, non-antibody protein scaffolds, etc.), and aptamers.

As used herein, the term "biological component" refers to any biological molecule of a cell. Exemplary biological components include, but are not limited to, proteins, epitopes, antigens, nucleic acids, carbohydrates, lipids, and small molecules. Target biological components are those biological components that have a specific affinity for a binding element used in a method described herein or present in a composition described herein.

As used herein, the term "level" in the context of a level of a target biological component (e.g., a target protein) refers to a presence, absence, or amount of the target biological component. Thus, determining a level of a biological component refers to determining the presence, absence, or amount of the biological component.

As used herein, the term "partitioning" or "partitioned" refers to separating a sample into a plurality of portions, or "partitions." Partitions can be solid or fluid. In some embodiments, a partition is a solid partition, e.g., a micro channel. In some embodiments, a partition is a fluid partition, e.g., a droplet. In some embodiments, a fluid partition (e.g., a droplet) is a mixture of immiscible fluids (e.g., water and oil), or an emulsion. In some embodiments, a fluid partition (e.g., a droplet) is an aqueous droplet that is surrounded by an immiscible carrier fluid (e.g., oil). In other embodiments, a fluid partition is an aqueous droplet that is physically or chemically separated from adjacent aqueous droplets such that the contents of one droplet does not diffuse into adjacent droplets.

In some cases partitions are virtual. In a preferred embodiment, virtual partitions require a physical alteration of a molecule or group of molecules, wherein the alteration identifies a unique partition for that molecule or group of molecules. Typical physical alterations suitable for establishing or maintaining virtual partitioning include, without limitation, nucleic acid barcodes, detectable labels, etc. For example, a sample can be physically partitioned, and the components of each partition tagged with a unique identifier (e.g., a unique nucleic acid sequence barcode) such that the identifier is unique as compared to other partitions but shared between the components of the partition. The unique identifier can then be used to maintain a virtual partition in downstream applications that involve combining of the physically partitioned material. Thus, if the sample is a sample of cells physically partitioned into partitions containing a single cell, the identifier can identify different nucleic acids that derived from a single cell after partitions are recombined.

The term "amplification reaction" refers to any in vitro means for multiplying the copies of a target sequence of nucleic acid in a linear or exponential manner. Such methods include but are not limited to polymerase chain reaction (PCR); DNA ligase chain reaction (see U.S. Pat. Nos. 4,683,195 and 4,683,202; PCR Protocols: A Guide to Methods and Applications (Innis et al., eds, 1990)) (LCR); QBeta RNA replicase and RNA transcription-based amplification reactions (e.g., amplification that involves T7, T3, or SP6 primed RNA polymerization), such as the transcription amplification system (TAS), nucleic acid sequence based amplification (NASBA), and self-sustained sequence replication (3 SR); isothermal amplification reactions (e.g., single-primer isothermal amplification (SPIA)); as well as others known to those of skill in the art.

"Amplifying" refers to a step of submitting a solution to conditions sufficient to allow for amplification of a polynucleotide if all of the components of the reaction are intact. Components of an amplification reaction include, e.g., one or more primers, a polynucleotide template, polymerase, nucleotides, and the like. The term "amplifying" typically refers to an "exponential" increase in target nucleic acid. However, "amplifying" as used herein can also refer to linear increases in the numbers of a select target sequence of nucleic acid, such as is obtained with cycle sequencing or linear amplification.

The term "amplification reaction mixture" refers to an aqueous solution comprising the various reagents used to amplify a target nucleic acid. These include enzymes, aqueous buffers, salts, one or more amplification primers, target nucleic acid, and nucleoside triphosphates. Amplification reaction mixtures may also further include stabilizers and other additives to optimize efficiency and specificity. Depending upon the context, the mixture can be either a complete or incomplete amplification reaction mixture.

"Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step.

A "primer" refers to a polynucleotide sequence that hybridizes to a sequence on a target nucleic acid and serves as a point of initiation of nucleic acid synthesis. Primers can be of a variety of lengths and are often less than 50 nucleotides in length, for example 12-30 nucleotides, in length. The length and sequences of primers for use in PCR can be designed based on principles known to those of skill in the art, see, e.g., Innis et al., supra. Primers can be DNA, RNA, or a chimera of DNA and RNA portions. In some cases, primers can include one or more modified or non-natural nucleotide bases. In some cases, primers are labeled.

A nucleic acid, or a portion thereof, "hybridizes" to another nucleic acid under conditions such that non-specific hybridization is minimal at a defined temperature in a physiological buffer (e.g., pH 6-9, 25-150 mM chloride salt). In some cases, a nucleic acid, or portion thereof, hybridizes to a conserved sequence shared among a group of target nucleic acids. In some cases, a primer, or portion thereof, can hybridize to a primer binding site if there are at least about 6, 7, 8, 9, 10, 11, 12, 13, 14, 15, 16, 17, or 18 contiguous complementary nucleotides, including "universal" nucleotides that are complementary to more than one nucleotide partner. In some cases, a primer, or portion thereof, can hybridize to a primer binding site if there are fewer than 0, 1, or 2 complementarity mismatches over at least about 12, 13, 14, 15, 16, 17, or 18 contiguous nucleotides. In some embodiments, the defined temperature at which specific hybridization occurs is room temperature. In some embodiments, the defined temperature at which specific hybridization occurs is higher than room temperature. In some embodiments, the defined temperature at which specific hybridization occurs is at least about 37, 40, 42, 45, 50, 55, 60, 65, 68, 70, 72, or 75° C. In some embodiments, the defined temperature at which specific hybridization occurs is 37, 40, 42, 45, 50, 55, 60, 65, 68, 70, 72, or 75° C.

A "template" refers to a polynucleotide sequence that comprises the polynucleotide to be amplified, flanked by a pair of primer hybridization sites or adjacent to a primer hybridization site. Thus, a "target template" comprises the target polynucleotide sequence adjacent to at least one hybridization site for a primer. In some cases, a "target template" comprises the target polynucleotide sequence flanked by a hybridization site for a "forward" primer and a "reverse" primer. The target template can be single-stranded or double-stranded. The target can be single-stranded and become double-stranded after hybridizing and extension of a first (e.g., forward or reverse) primer.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications including but not limited to capping with a fluorophore (e.g., quantum dot or fluorescent organic dye) or another moiety.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

A "polymerase" refers to an enzyme that performs template-directed synthesis of polynucleotides, e.g., DNA and/or RNA. The term encompasses both the full length polypeptide and a domain that has polymerase activity. DNA polymerases are well-known to those skilled in the art, including but not limited to DNA polymerases isolated or derived from *Pyrococcus furiosus, Thermococcus litoralis,* and *Thermotoga maritime,* or modified versions thereof. Additional examples of commercially available polymerase enzymes include, but are not limited to: Klenow fragment (New England Biolabs® Inc.), Taq DNA polymerase (QIAGEN), 9° N™ DNA polymerase (New England Biolabs® Inc.), Deep Vent™ DNA polymerase (New England Biolabs® Inc.), Manta DNA polymerase (Enzymatics®), Bst DNA polymerase (New England Biolabs® Inc.), and phi29 DNA polymerase (New England Biolabs® Inc.).

Polymerases include both DNA-dependent polymerases and RNA-dependent polymerases such as reverse transcriptase. At least five families of DNA-dependent DNA polymerases are known, although most fall into families A, B and C. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent.

The terms "label," "detectable label, "detectable moiety," and like terms refer to a composition detectable by spectroscopic, photochemical, biochemical, immunochemical, chemical, or other physical means. For example, useful labels include fluorescent dyes (fluorophores), luminescent agents, electron-dense reagents, enzymes (e.g., as commonly used in an ELISA), biotin, digoxigenin, $^{32}P$ and other isotopes, haptens, and proteins which can be made detectable, e.g., by incorporating a radiolabel into the peptide or used to detect antibodies specifically reactive with the peptide. The term includes combinations of single labeling agents, e.g., a combination of fluorophores that provides a unique detectable signature, e.g., at a particular wavelength or combination of wavelengths. Any method known in the art for conjugating label to a desired agent may be employed, e.g., using methods described in Hermanson, *Bioconjugate Techniques* 1996, Academic Press, Inc., San Diego.

As used herein a "barcode" is a short nucleotide sequence (e.g., at least about 4, 6, 8, 10, or 12, nucleotides long) that identifies a molecule to which it is conjugated. In some cases, an oligonucleotide encoding a target ID barcode can be conjugated to a binding element (e.g., antibody). Binding of the binding element to its corresponding target can be detected by detecting the presence of the target ID barcode. Thus the level of the target biological component can be determined by detecting the number of oligonucleotides containing the target ID barcode. Similarly, a plurality of structurally different binding elements (e.g., antibodies) that each bind a different structurally different target biological component can be conjugated to a plurality of oligonucleotides containing target ID barcodes, a different barcode for each structurally different binding element. Thus the level of a plurality of target biological components can be determined by detecting the number of oligonucleotides containing each of the corresponding target ID barcodes. Partitions containing target RNA from single-cells can subject to reverse transcription conditions using primers that contain a different partition-specific barcode sequence in each partition, thus incorporating a copy of a unique "cellular barcode" into the reverse transcribed nucleic acids of each partition. Thus, nucleic acid from each cell can be distinguished from nucleic acid of other cells due to the unique "cellular barcode."

In some cases, barcodes can be used, e.g., to identify molecules in a partition. Such a partition-specific barcode should be unique for that partition as compared to partition-specific barcodes present in other partitions. For example, partitions containing target biological components (e.g., proteins) from single-cells can contain a different partition-specific barcode sequence in each partition. The partition-specific barcode can be used to label the oligonucleotides that contain the target ID barcodes and are conjugated to the binding elements in the partitions. Therefore a copy of a unique "cellular barcode" can be incorporated into the target ID oligonucleotide tags of each partition. Consequently, the target biological component levels (e.g., presence, absence, or amount) from each cell can be distinguished from target biological component levels from other cells due to the unique "cellular barcode."

The cellular barcode can be provided by a "particle barcode" that is present on oligonucleotides conjugated to a particle, wherein the particle barcode is shared by (e.g., identical or substantially identical amongst) all, or substantially all, of the oligonucleotides conjugated to that particle and different from the oligonucleotides conjugated to other particles in a plurality of partitions. Thus, cellular and particle barcodes can be present in a partition, attached to a particle, or incorporated into oligonucleotides encoding a target ID. Cellular or particle barcodes of the same sequence can be identified as deriving from the same cell, partition, and/or particle. Such partition-specific, cellular, or particle barcodes can be generated using a variety of methods, including but not limited to, methods that result in the barcode conjugated to or incorporated into a solid or hydrogel support (e.g., a solid bead or particle or hydrogel bead or particle). In some cases, the hydrogel support is or contains cross-linked agarose. In some cases, the partition-specific, cellular, or particle barcode is generated using a split and mix (also referred to as split and pool) synthetic scheme. A partition-specific barcode can be a cellular barcode and/or a particle barcode. Similarly, a cellular barcode can be a partition specific barcode and/or a particle barcode. Additionally, a particle barcode can be a cellular barcode and/or a partition-specific barcode.

In some cases, barcodes uniquely identify the molecule to which it is conjugated. Such a barcode is commonly known as a "unique molecular identifier" (UMIs). In some cases, primers and/or oligonucleotides can be utilized that contain "partition-specific barcodes" unique to each partition, target IDs, unique to each target a binding element has a specific affinity for, and UMIs unique to each molecule. After barcoding, partitions can then be combined, and optionally amplified, while maintaining virtual partitioning. Thus, e.g., the number of each oligonucleotide comprising each barcode can be counted (e.g. by sequencing) to provide the level of each target biological component without the necessity of maintaining physical partitions.

The length of the barcode sequence determines how many unique samples can be differentiated. For example, a 1 nucleotide barcode can differentiate 4, or fewer, different samples or molecules; a 4 nucleotide barcode can differentiate $4^4$ or 256 samples or less; a 6 nucleotide barcode can differentiate 4096 different samples or less; and an 8 nucleotide barcode can index 65,536 different samples or less. Additionally, barcodes can be attached to both strands of a single stranded oligonucleotide either through amplification with barcoded primers or through ligation.

Barcodes are typically synthesized and/or polymerized (e.g., amplified) using processes that are inherently inexact. Thus, barcodes that are meant to be uniform (e.g., a cellular, particle, or partition-specific barcode shared amongst all barcoded nucleic acid of a single partition, cell, or bead) can contain various N-1 deletions or other mutations from the canonical barcode sequence. Thus, barcodes that are referred to as "identical or substantially identical copies" refer to barcodes that differ due to one or more errors in, e.g., synthesis, polymerization, or purification and thus contain various N-1 deletions or other mutations from the canonical barcode sequence. Moreover, the random conjugation of barcode nucleotides during synthesis using e.g., a split and pool approach and/or an equal mixture of nucleotide precursor molecules as described herein, can lead to low probability events in which a barcode is not absolutely unique (e.g., different from other barcodes of a population or different from barcodes of a different partition, cell, or bead). However, such minor variations from theoretically ideal barcodes do not interfere with the single cell analysis methods, compositions, and kits described herein. Therefore, as used herein, the term "unique" in the context of a particle, cellular, partition-specific, or molecular barcode encompasses various inadvertent N−1 deletions and mutations from the ideal barcode sequence. In some cases, issues due to the inexact nature of barcode synthesis, polymerization, and/or amplification, are overcome by oversampling of possible barcode sequences as compared to the number of barcode sequences to be distinguished (e.g., at least about 2-, 5-, 10-fold or more possible barcode sequences). For example, 10,000 cells can be analyzed using a cellular barcode having 9 barcode nucleotides, representing 262,144 possible barcode sequences. The use of barcode technology is well known in the art, see for example Katsuyuki Shiroguchi, et al. Proc Natl Acad Sci USA., 2012 Jan. 24; 109(4):1347-52; and Smith, A M et al., Nucleic Acids Research Can 11, (2010).

DETAILED DESCRIPTION OF THE INVENTION

I. Overview

Described herein are compositions, methods, and kits for performing quantitative analysis of target biological components. The compositions, methods, and kits described herein can be used to determine the level of a plurality target biological components of a plurality of cells at single-cell resolution. The compositions, methods, and kits described herein are based on the principal that the level of a target biological component can be encoded into an oligonucleotide. The oligonucleotide to be encoded is conjugated to a binding element specific for that target biological component. The conjugated oligonucleotide includes a target ID sequence that corresponds to the target biological component. The encoding can be performed by a binding event between the target biological component and the binding element. Detection of the target ID sequence of the encoded oligonucleotide detects the target biological component, if present. High throughput sequencing of a plurality of encoded oligonucleotides can be performed to count the number of oligonucleotides encoding the target ID sequence, thereby determining the level of the target biological component. The method can be performed in parallel with, e.g., from 2 to about 10,000 or more, structurally different binding elements that specifically bind structurally different target biological components. Each structurally different binding element can be conjugated to an oligonucleotide with a different target ID sequence. The method can further be performed in parallel with from 2 to about 10,000 or more different single cells. Therefore, the methods, compositions, and kits described herein can be useful for, e.g., quantitative analysis, at single-cell resolution, of a large number target biological components in a large number of single cells.

II. Compositions a. Fixed and Permeabilized Cells

Described herein are fixed (e.g., cross-linked) and permeabilized cells. The fixed and permeabilized cells can contain a plurality of target biological components of the cell. Thus the fixed and permeabilized cells can be analyzed, according to methods described herein, to determine the levels of the plurality of target biological components. The fixed and permeabilized cells can be fixed and permeabilized by any method suitable to render the target biological components of the fixed and permeabilized cells resistant to washing away and accessible to target binding elements. Such methods include, but are not limited to, cell fixation and permeabilization methods described in further detail below, and variations thereof.

b. Barcodes and Oligonucleotides Containing Such Barcodes

Described herein are target ID barcodes and oligonucleotides that contain a target ID barcode. A target ID barcode contains a nucleic acid sequence that is unique to the target ID barcode and thus unique to the corresponding target biological component and different from all other target ID barcodes that correspond to other target biological components. The target ID barcode can be as short as a single nucleotide, or as long as 20 nucleotides in length, or longer. In an exemplary embodiment, the target ID barcode is 6-8 nucleotides in length. Generally, the length of the target ID barcode sequence determines the number of different target biological components that can be analyzed in a single sequencing run. For example, a target ID barcode having a single nucleotide that can be any one of the standard four DNA bases (A, G, C, or T), can be used to analyze four or fewer different target biological components. Similarly, a target ID barcode having a length of four nucleotides can be used to analyze $4^4$ (256) or fewer different target biological components. An oligonucleotide that contains a target ID barcode can be a component of a sequencing library, a conjugation library, a binding element library, and/or a plurality of partitions. In some cases, an oligonucleotide containing a target ID barcode is conjugated to a binding element (e.g., antibody) that specifically binds a target biological component (e.g., protein).

Also described herein are partition-specific barcodes and oligonucleotides containing such partition-specific barcodes. A partition-specific barcode contains a nucleic acid sequence that is unique to a partition and different from all other partition-specific barcodes in other partitions. In some cases, the partitions-specific barcode is also, or is used to label one or more target biological components with, a cellular barcode. For example, a partition-specific barcode can be present in a partition that contains a single fixed and permeabilized cell. The target biological components of the fixed and permeabilized cell can be labeled with the partition-specific barcode, thus labeling all the target biological components as having derived from the same single cell. Similarly, a partition-specific barcode can be present in a partition that contains a single fixed and permeabilized cell and a plurality of binding elements bound to target biological components of the cell. The binding elements can be labeled with the partition-specific barcode, thus labeling all the binding elements as encoding information about the target biological components from the same single cell. Such information can be the level of the target biological components from the same single cell.

The partition-specific barcode can be as short as a single nucleotide, or as long as 20 nucleotides in length, or longer. In an exemplary embodiment, the partition-specific barcode is 6-8 nucleotides in length. Generally, the length of the partition-specific barcode sequence determines the number of different fixed and permeabilized cells that can be analyzed in a single sequencing run. For example, a partition-specific barcode having a single nucleotide that can be any one of the standard four DNA bases (A, G, C, or T), can be used to analyze four or fewer different fixed and permeabilized cells. Similarly, a partition-specific barcode having a length of four nucleotides can be used to analyze $4^4$ (256) or fewer different fixed and permeabilized cells. An oligonucleotide that contains a partition-specific barcode can be a component of a solid surface (e.g., bead) with a plurality of copies of an oligonucleotide containing the partition-specific barcode immobilized thereon. Similarly, a partition-specific barcode can be a component of a sequencing library, and/or a plurality of partitions. In some cases, an oligonucleotide containing a partition-specific barcode is conjugated to a binding element (e.g., antibody) that specifically binds a target biological component (e.g., protein). In some cases, an oligonucleotide containing a partition-specific barcode is hybridized to an oligonucleotide that is conjugated to a binding element (e.g., antibody) that specifically binds a target biological component (e.g., protein).

Also described herein are universal molecular identifier (UMI) barcodes and oligonucleotides containing such UMIs. A UMI contains a nucleic acid sequence that is unique and therefore different from all other UMIs. In some cases, the UMI is unique and therefore different from all other UMIs in the same partition or derived from the same single fixed and permeabilized cell. For example, a set of UMIs need not be unique as compared to UMIs in a different partition if the UMIs are paired with a partition-specific barcode sequence, or will be paired with a partition-specific barcode sequence in a subsequent step, as the combination of the partition-specific barcode and the UMI can be unique as compared to all other such combinations. Similarly, a set of UMIs need not be unique as compared to UMIs associated with a different target ID barcode if the UMIs are paired with a target ID barcode sequence, as the combination of the target ID barcode and the UMI can be unique as compared to all other such combinations.

An oligonucleotide that contains a UMI barcode can be a component of a sequencing library, a conjugation library, a binding element library, and/or a plurality of partitions. In some cases, an oligonucleotide containing a UMI barcode is conjugated to a binding element (e.g., antibody) that specifically binds a target biological component (e.g., protein). The oligonucleotide containing the UMI barcode can also contain a partition-specific barcode, target ID barcode, or a combination thereof. The UMI, e.g., in combination with a partition-specific barcode and/or target ID barcode, can identify a nucleic acid molecule as unique or as an amplification copy. For example, in a pair of oligonucleotides that contain identical target ID barcode, partition-specific barcode, and UMI barcode sequences, it is likely that one of the oligonucleotides is an amplification copy of the other oligonucleotide or both oligonucleotides are amplification copies of a third oligonucleotide. Similarly, in a pair of oligonucleotides that contain identical target ID barcode and partition-specific barcode sequences, but different UMI barcode sequences, it is likely that both oligonucleotides indicate the presence of a different corresponding target biological component molecule of the corresponding same single cell.

The UMI barcode can be as short as a single nucleotide, or as long as 20 nucleotides in length, or longer. In an exemplary embodiment, the UMI barcode is 6-8 nucleotides in length. Generally, the length of the UMI barcode sequence if present, e.g., in combination with the target ID barcode sequence and/or partition-specific barcode sequence, determines the number of different molecules that can be analyzed in a single sequencing run. For example, a UMI barcode having a single nucleotide that can be any one of the standard four DNA bases (A, G, C, or T), can be used to analyze four or fewer different molecules corresponding to a single target biological component and/or single cell. Similarly, a target ID barcode having a length of four nucleotides can be used to analyze $4^4$ (256) or fewer different molecules corresponding to a single target biological component and/or single cell.

An oligonucleotide can contain one or more of the target ID barcode, the partition-specific barcode, the UMI barcode, or a combination thereof. Such oligonucleotides can contain these barcodes in any suitable order relative to one another and/or relative to other regions of the oligonucleotides. In one embodiment, the oligonucleotide is single-stranded, and contains from 5' to 3' a partition-specific barcode, a target ID barcode, and optionally a UMI barcode. In another embodiment, the oligonucleotide is single-stranded, and contains from 5' to 3' a partition-specific barcode, an optional UMI barcode, and a target ID barcode. In another embodiment, the oligonucleotide is single-stranded, and contains from 5' to 3' a target ID barcode, a partition-specific barcode, and optionally a UMI barcode. In another embodiment, the oligonucleotide is single-stranded, and contains from 5' to 3' a target ID barcode, an optional UMI barcode, and a partition-specific barcode. In another embodiment, the oligonucleotide is single-stranded, and contains from 5' to 3' an optional UMI barcode, a partition-specific barcode, and a target ID barcode. In another embodiment, the oligonucleotide is single-stranded, and contains from 5' to 3' an optional UMI barcode, a target ID barcode, and partition-specific barcode.

In any of the foregoing embodiments, the single-stranded oligonucleotide can contain a sample index barcode. The sample index can be at any position relative to a target ID barcode, UMI barcode, or partition-specific barcode, if present. For example, the sample index can be 5' of the partition-specific barcode. Alternatively, the sample index can be 3' of the partition-specific barcode. In some cases, the sample index is 5' of the UMI barcode, if present. In some cases, the sample index is 3' of the UMI barcode, if present. In some cases, the sample index is 5' of the target ID barcode. In some cases, the sample index is 3' of the target ID barcode.

The sample index barcode can identify a source of a particular nucleic acid, thereby allowing multiplex analysis of a plurality of samples. For example, a plurality of samples, each containing a plurality of fixed and permeabilized single-cells, can be simultaneously analyzed using the methods described herein. The sample index can be detected and used to identify which oligonucleotide sequences correspond to which samples. The plurality of samples can be from a single subject, e.g., collected or provided at multiple time points or from multiple different tissues. The plurality of samples can be from different subjects, e.g., different human subjects.

The sample index barcode can be as short as a single nucleotide, or as long as 20 nucleotides in length, or longer. In an exemplary embodiment, the sample index barcode is 2, 3, or 4 nucleotides in length. Generally, the length of the sample index barcode sequence if present, determines the number of different samples that can be analyzed in a single sequencing run. For example, a sample index barcode having a single nucleotide that can be any one of the standard four DNA bases (A, G, C, or T), can be used to analyze four or fewer different samples. Similarly, a sample index barcode having a length of 2 nucleotides can be used to analyze $4^2$ (16) or fewer different samples.

In any of the foregoing embodiments, the single-stranded oligonucleotide can contain a universal primer binding sequence at a 5' or 3' end. The universal primer binding sequence can be complementary to a universal primer present in a partition. In some cases, the single-stranded oligonucleotide can contain a primer binding sequence at a 5' end that is complementary to a first primer, or contain the reverse complement thereof, and a different primer binding sequence at a 3' end that is complementary to a second primer, or contain the reverse complement thereof. The first and/or second primer can be present in a partition that contains the single-stranded oligonucleotide. The first or second primer can contain a partition-specific barcode sequence, a sample index barcode sequence, and/or a UMI barcode sequence. The first or second primer can contain, or contain a region that is complementary to, a high-throughput sequencing library adaptor sequence (e.g., P5, Read 1, P7, Read 2, etc.), or a portion thereof.

Any one of the foregoing single-stranded oligonucleotides can be conjugated to a binding element such as an antibody, e.g., at a 5' or 3' end of the single-stranded oligonucleotide. The single-stranded oligonucleotide can be conjugated to a binding element via cleavable linker. The cleavable linker can be a nucleic acid sequence that contains a restriction endonuclease recognition site. Alternatively, the cleavable linker can be a nucleic acid sequence that contains a uracil, and thereby be cleavable with a uracil-DNA glycosylase enzyme. Alternatively, the cleavable linker can be cleavable by other enzymatic means. As yet another alternative, the cleavable linker can contain a region that is cleavable by chemical means. For example, the cleavable linker can contain a disulfide bond that is cleavable with a reducing agent (e.g., dithiothreitol or triscarboxyethylphosphine).

As described herein, single-stranded oligonucleotides containing a partition-specific barcode sequence (i.e., partition-specific barcoded oligonucleotides) can be covalently immobilized on a solid surface, such as a bead. Such partition-specific barcode oligonucleotides can further contain primer and/or high throughput sequencing adaptor sequences at the 5' and/or 3' end, reverse complements thereof, or portions thereof. The partition-specific barcode oligonucleotide can be covalently linked at a 5' or 3' end to a bead, e.g., with a cleavable linker. The cleavable linker can be a nucleic acid sequence that contains a restriction endonuclease recognition site. Alternatively, the cleavable linker can be a nucleic acid sequence that contains a uracil, and thereby be cleavable with a uracil-DNA glycosylase enzyme. Alternatively, the cleavable linker can be cleavable by other enzymatic means. As yet another alternative, the cleavable linker can contain a region that is cleavable by chemical means. For example, the cleavable linker can contain a disulfide bond that is cleavable with a reducing agent (e.g., dithiothreitol or triscarboxyethylphosphine).

As yet another alternative, the partition-specific barcoded oligonucleotides can be conjugated to a meltable bead, such as a thermally reversible hydrogel bead (e.g., a bead containing cross-linked agarose). In some cases, the meltable bead can be melted by heating, wherein the melting dissolves one or more solid surface components of the bead into other components of a mixture in which the bead resides such that subsequent cooling of the bead does not reform the solid surface. Thus, in some embodiments, partition-specific barcoded oligonucleotides can be released by heating rather than cleaving.

Similarly, in another alternative, partition-specific barcoded oligonucleotides can be conjugated to a solid surface comprising a polymer (e.g., a cross-linked polymer) that can be depolymerized or un-cross-linked by chemical or enzymatic means to release partition-specific barcoded oligonucleotides. For example, partition-specific barcoded oligonucleotides can be conjugated to a bead comprised of a disulfide cross-linked polymer and the partition-specific barcoded oligonucleotides can be released by contact with a reducing agent. As another example, partition-specific barcoded oligonucleotides can be conjugated to an agarose bead, and the partition-specific barcoded oligonucleotides can be released by contact with an agarase. Exemplary solid surfaces covalently linked to oligonucleotides containing partition-specific barcodes include those described in PCT Appl. Serial No. PCT/US15/37525, filed on Jun. 24, 2015, the contents of which are hereby incorporated by reference in the entirety for all purposes and in particular for disclosure related to beads, oligonucleotide conjugated beads, and methods of preparing and using such beads or oligonucleotide conjugated beads.

Any one of the foregoing single-stranded oligonucleotides can be hybridized to a complementary, or partially complementary oligonucleotide. For example, any one of the foregoing single-stranded oligonucleotides can be hybridized to its reverse complement, forming a double-stranded oligonucleotide. As another example, any one of the foregoing single-stranded oligonucleotides can be hybridized to an oligonucleotide primer, which primer can be fully or partially complementary at least a portion of the single-stranded oligonucleotides. In some cases, the primer can contain one or more barcode sequences such as a UMI barcode sequence, or a partition-specific barcode sequence. In some cases, the primer can contain one or more high-throughput sequencing library adaptor sequences, or portions thereof. In some cases, the primer can contain a 3' region that specifically hybridizes to a universal sequence at a 5' or 3' end of the single stranded oligonucleotide. In some cases, a primer can contain a 3' region that specifically hybridizes to a universal sequence that is complementary to a sequence at a 5' or 3' end of the single stranded oligonucleotide. Thus, for example, a first primer (or 3' region thereof) can hybridize to a primer binding site at a 5' end of the single-stranded oligonucleotide and be extended by a polymerase to generate, on the resulting primer extension product, a primer binding site for a second primer (or 3' region thereof).

c. Libraries

Described herein are sequencing libraries and conjugation libraries. Such libraries generally contain a plurality of one or more of the foregoing barcode oligonucleotides (oligonucleotides containing one or more barcode sequences). Also described herein are binding element libraries. In some cases, individual binding elements of a binding element library are conjugated to barcode oligonucleotides, e.g., via cleavable linker. Also described herein are partition-specific barcode libraries. In some cases, the partition-specific barcode library contains a plurality partition-specific barcoded oligonucleotides conjugated to a plurality of solid surfaces. Any one or more of the libraries described herein can be present in a partition, or in a plurality of partitions.

Sequencing libraries described herein contain a plurality of oligonucleotides configured to be compatible with one or more high-throughput sequencing platforms. As such, the oligonucleotides of the sequencing libraries can contain at least one high-throughput sequencing adaptor sequence at a 5' or 3' end. In some cases, the oligonucleotides can contain a first high-throughput sequencing adaptor sequence at a 5' end and a second different high-throughput sequencing adaptor sequence at a 3' end. In some cases, the oligonucleotides contain a P5 Illumina adaptor sequence at one end and a P7 Illumina adaptor sequence at the other end. The oligonucleotides of the sequencing library can be single- or double-stranded.

Generally, the oligonucleotide components of the sequencing library each contain a partition-specific barcode and a target ID barcode. In some cases, the oligonucleotides of the sequencing library additionally contain a UMI barcode. In some embodiments, the oligonucleotides of the sequencing library contain a sample index sequence. In some cases, the sample index is the same for all oligonucleotides of the sequencing library. In some cases, multiple sequencing libraries, each composed of oligonucleotides that contain a uniform sample index, wherein the uniform sample index is different among the different multiple sequencing libraries, can be mixed together to simultaneously analyze sequencing libraries corresponding to multiple samples.

Partition-specific barcode libraries described herein can contain a plurality of oligonucleotides that share identical first partition-specific barcode sequences, a plurality of oligonucleotides that share identical second partition-specific barcode sequences, a plurality of oligonucleotides that share identical third partition-specific barcode sequences, etc., wherein each first, second, third, etc., plurality contains partition specific barcode sequences that differ from each other. The partition-specific barcode library can contain 2; 3; 4; 5; 6; 7; 8; 9; 10; 11; 12; 13; 14; 15; 16; 17; 18; 19; 20; 22; 25; 30; 35; 40; 50; 60; 70; 80; 90; 100; 200; 300; 500; 750; 1000; 2500; 5000; 7500; 10,000; 15,000; 20,000; 30,000; 40,000; 50,000; 60,000; 70,000; 80,000; 100,000; 125,000; 150,000; 175,000; 200,000; 250,000, or more different barcode sequences, each sequence present in a plurality of identical oligonucleotide copies. In some cases, each plurality of identical oligonucleotide copy comprises at least, or comprises at least about, 10; 11; 12; 13; 14; 15; 16; 17; 18; 19; 20; 22; 25; 30; 35; 40; 50; 60; 70; 80; 90; 100; 200; 300; 500; 750; 1000; 2500; 5000; 7500; 10,000; 15,000; 20,000; 30,000; 50,000; 60,000; 70,000; 80,000; 90,000; 100,000; 125,000; 150,000; 175,000; 200,000; 250,000, 300,000; 400,000; 500,000; 750,000; $10^6$, $10^7$, $10^8$, $10^9$, or more identical oligonucleotide copies. In some cases each plurality of oligonucleotides conjugated to a shared solid surface shares an identical partition-specific barcode sequence that is different from all other partition-specific barcode sequences of the library. In some cases each plurality of oligonucleotides present in the same partition shares an identical partition-specific barcode sequence that is different from all other partition-specific barcode sequences of the library.

Binding element libraries described herein include antibody libraries, antibody fragment libraries, aptamer libraries, and the like, including libraries that contain mixtures of two or more of antibodies, antibody fragments, aptamers, and the like. The binding element libraries can contain from about 2 to about 100,000 or more structurally different binding elements, from about 2 to about 50,000 or more structurally different binding elements, from about 2 to about 10,000 or more structurally different binding elements, from about 10 to about 5,000 structurally different binding elements, from about 10 to about 1,000 structurally different binding elements, from about 10 to about 500 structurally different binding elements, or from about 10 to about 100 structurally different binding elements, e.g., about 2; 3; 4; 5; 6; 7; 8; 9; 10; 11; 12; 13; 14; 15; 16; 17; 18; 19; 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56; 57; 58; 59; 60; 61; 62; 63; 70; 80; 90; 100; 200; 300; 500; 750; 1,000; 2,500; 5,000; 7,500; 10,000; 15,000; 20,000; 30,000; 50,000; 75,000; 100,000, or more structurally different elements. In some cases, each structurally different binding element specifically binds a different target biological component.

In some cases, a majority (e.g., greater than at least 50%, at least 75%, at least 90%, or at least 99%) of each of the structurally different binding elements specifically bind a different target biological component. In some cases, multiple structurally different binding elements can be present as internal controls, such that detection of, or about, the same level of a target biological component using two different structurally different binding elements that specifically bind the same target biological component can provide increased statistical confidence or decreased data variability in one or more of the methods described herein. In some cases, about 1%, 5%, 10%, 15%, 20%, 25%, 30%, 35%, 40%, 45%, 50%, 55%, 60%, 65%, 70%, 75%, 80%, 90%, 95%, or 100% of the structurally different binding elements specifically binds a target biological component that is also recognized by at least one other structurally different binding element of the library. In some cases, components of the library of binding elements are conjugated to barcoded oligonucleotides. For example, components of the library of binding elements (e.g., antibody components) can each be conjugated to an oligonucleotide that contains a target ID barcode sequence and optionally a UMI barcode sequence. In some cases, the conjugated oligonucleotide further contains a partition-specific barcode sequence.

Conjugation libraries described herein contain a plurality of target ID barcoded oligonucleotides that can be used to tag a library of binding elements with a target ID barcode, optionally in combination with one or more of the other barcodes described herein such as a UMI barcode, a partition-specific barcode, a sample index barcode, and combinations thereof. Individual oligonucleotides of the conjugation library can contain a reactive moiety configured to form a covalent link (e.g., covalent cleavable link) with a binding element. In some cases, the conjugation library is provided in an addressably partitioned format such that each partition contains one or more oligonucleotides that share an identical target ID barcode sequence that is different from the target ID barcode sequences in all other partitions, where the target ID barcode sequence in each partition is known.

In some cases, the conjugation library is present in multiple wells of a multi-well plate, or multiple reaction chambers of a multi-reaction chamber device. A library of binding elements can be partitioned into the reaction chambers such that each reaction chamber contains a plurality of structurally identical binding elements that specifically bind a known target biological component, and a plurality of oligonucleotides that share an identical target ID barcode. In some cases, a library of binding elements can be partitioned into the reaction chambers such that each reaction chamber contains a plurality of binding elements that specifically bind a known target biological component, and a plurality of oligonucleotides that share an identical target ID barcode. The conjugation between the binding elements and the oligonucleotides of the conjugation library can thereby be performed in the partitions to generate a library of target ID barcode tagged binding elements, where the target ID barcode sequence and corresponding target biological component that the binding element specifically binds are known.

The oligonucleotides of the conjugation library can contain additional primer binding sequences, adaptor sequences, or combinations thereof. In some cases, the oligonucleotides of the conjugation library contain a 3' primer binding sequence at a 3' end and a reverse complement of a 5' primer binding sequence at a 5' end. In some cases, a primer binding sequence, or reverse complement thereof at the 5' or 3' end, can contain a high-throughput sequencing adaptor sequence or a reverse complement thereof. In some cases, the oligonucleotides of the conjugation library are single-stranded. In some cases, the oligonucleotides of the conjugation library are double-stranded.

The conjugation library can contain a plurality of oligonucleotides, wherein each oligonucleotide contains 1 target ID barcode, and wherein the plurality of oligonucleotides of the conjugation library include from about 2 to about 100,000 or more structurally different target ID barcodes, from about 2 to about 50,000 or more structurally different target ID barcodes, from about 2 to about 10,000 or more structurally different target ID barcodes, from about 10 to about 5,000 structurally different target ID barcodes, from about 10 to about 1,000 structurally different target ID barcodes, from about 10 to about 500 structurally different target ID barcodes, or from about 10 to about 100 structurally different target ID barcodes, e.g., about 2; 3; 4; 5; 6; 7; 8; 9; 10; 11; 12; 13; 14; 15; 16; 17; 18; 19; 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56; 57; 58; 59; 60; 61; 62; 63; 70; 80; 90; 100; 200; 300; 500; 750; 1,000; 2,500; 5,000; 7,500; 10,000; 15,000; 20,000; 30,000; 40,000; 50,000; 60,000; 65,536; 70,000; 75,000; 80,000; 90,000; 100,000, or more structurally different target ID barcodes.

d. Mixture Partitions

Described herein are pluralities of mixture partitions (e.g., at least 2, 3, 4, 5, 6, 7, 8, 9, 10, 11, 12, 13, 14, 15, 16, 17, 18, 19, 20, 22, 25, 30, 35, 40, 50, 60, 70, 80, 90, 100; 200; 300; 500; 750; 1000; 2500; 5000; 7500; 10,000; 15,000; 20,000; 30,000; 40,000; 50,000; 60,000; 70,000; 80,000; 90,000; 100,000; 125,000; 150,000; 175,000; 200,000; 250,000, 300,000; 400,000; 500,000; 750,000; $10^6$, $10^7$, or more partitions), each partition having a fixed and permeabilized cell. The partitions can further contain template directed nucleic acid polymerization reagents and/or template directed nucleic acid polymerization products. Exemplary template directed nucleic acid polymerization reagents include DNA template (e.g., barcoded oligonucleotide), polymerase (e.g., thermostable DNA-dependent polymerase), nucleotides, buffer, salts, oligonucleotide primers (e.g., universal and/or partition-specific barcoded primers), etc.

The mixture partitions can contain any one of the foregoing oligonucleotides, barcodes, binding elements, fixed and permeabilized cells, components thereof, libraries thereof, and/or combinations thereof. In some embodiments, the mixture partitions further each contain a library of binding elements. In some cases, the library of binding elements includes from about 2 to about 100,000 or more structurally different binding elements, from about 2 to about 50,000 or more structurally different binding elements, from about 2 to about 10,000 or more structurally different binding elements, from about 10 to about 5,000 structurally different binding elements, from about 10 to about 1,000 structurally different binding elements, from about 10 to about 500 structurally different binding elements, or from about 10 to about 100 structurally different binding elements, e.g., about 2; 3; 4; 5; 6; 7; 8; 9; 10; 11; 12; 13; 14; 15; 16; 17; 18; 19; 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56; 57; 58; 59; 60; 61; 62; 63; 70; 80; 90; 100; 200; 300; 500; 750; 1,000; 2,500; 5,000; 7,500; 10,000; 15,000; 20,000; 30,000; 50,000; 75,000; 100,000, or more structurally different elements. In some cases, the binding elements are specifically bound to the target biological components, if present, of the single cells in each partition. For example, the library of binding elements can be a library of structurally different antibodies, wherein the structurally distinct antibodies have a specific binding affinity for, and are bound to, structurally distinct target epitopes of the proteins of the fixed and permeabilized cell in each partition.

The library of binding elements in the plurality of mixture partitions can be conjugated to target-epitope specific oligonucleotides (i.e., oligonucleotides that contain a target ID barcode sequence) with an optionally cleavable linker. In some cases, the cleavable linkers between the binding elements and the barcoded oligonucleotides are selected from the group consisting of linkers comprising a uracil nucleotide, linkers comprising a disulfide linkage, linkers comprising a restriction endonuclease cleavage site, and combinations thereof. Alternatively, the plurality of mixture partitions can contain the library of binding elements and a plurality of oligonucleotides that contain a target ID barcode sequence (i.e., target ID barcoded oligonucleotides) and have been cleaved from the binding elements of the library. The target ID barcoded oligonucleotides can further contain a UMI barcode. In some cases, the target-ID specific barcode sequences (e.g., target-epitope specific barcode sequences) are at least 4 nucleotides and no more than 15 nucleotides in length. In some cases, the UMI barcode is at least 4 nucleotides and no more than 15 nucleotides in length, or 6-8 nucleotides in length.

In some embodiments, the individual mixture partitions of the plurality of mixture partitions contain a plurality of partition-specific oligonucleotides, the individual partition-specific oligonucleotides containing a partition-specific barcode sequence that is identical among all partition-specific oligonucleotides of any one mixture partition and different from all partition-specific barcode sequences in other mixture partitions of the plurality. In some cases, the partition-specific barcoded oligonucleotides can further contain a UMI barcode. In some cases, the UMI barcode is at least 4 nucleotides and no more than 15 nucleotides in length, or 6-8 nucleotides in length. In some cases, the partition-specific barcoded oligonucleotides in an individual partition are covalently linked to a bead (e.g., a single bead) or other solid support surface and the plurality of mixture partitions each contain a bead (e.g., a single bead) or other solid support surface covalently linked to the partition-specific barcoded oligonucleotides in that partition.

In some cases, the partition-specific oligonucleotides are covalently linked to cross-linked agarose beads. In some cases, the cleavable linkers between the partition-specific barcoded oligonucleotides and the solid surface are selected from the group consisting of linkers comprising a uracil nucleotide, linkers comprising a disulfide linkage, linkers comprising a restriction endonuclease cleavage site, and combinations thereof. Alternatively, the partition-specific barcoded oligonucleotides can be cleaved from the or otherwise released from the beads or other solid support surfaces in the mixture partitions.

The plurality of mixture partitions can further contain a universal primer. In some cases, the universal primer contains a 3' priming region that hybridizes to a universal primer binding site of the oligonucleotides that contain a target ID barcode sequence, or a reverse complement thereof. In some cases, the universal primer can further contain a UMI barcode. In some cases, the UMI barcode is at least 4 nucleotides and no more than 15 nucleotides in length, or 6-8 nucleotides in length.

In some cases, the mixture partitions of the plurality of mixture partitions each contain a plurality of partition-specific oligonucleotides, wherein the specific oligonucleotides further contain a 3' priming region that hybridizes to a partition-specific oligonucleotide primer binding site of the target-epitope specific oligonucleotides, or reverse complements thereof In some cases, the 3' priming region of the partition-specific oligonucleotides is at least 12 and no more than 25 nucleotides in length. In some cases, the universal priming sequence of the 3' priming region of the universal primer is at least 12 and no more than 25 nucleotides in length In some cases, the 3' universal primer binding site and the partition-specific oligonucleotide primer binding site of the target-epitope specific oligonucleotides are on opposite strands of a double stranded target-epitope specific oligonucleotide and flank the target-epitope specific barcode sequence, and optionally the unique molecular identifier sequence.

In an exemplary embodiment, the individual plurality of mixture partitions contain i) a plurality of fixed proteins, wherein all of the fixed proteins in the individual mixture partition are from one cell; ii) a library of at least about 10 structurally distinct antibodies, wherein the structurally distinct antibodies have a specific binding affinity for, and are bound to, structurally distinct target epitopes of the fixed proteins; iii) a plurality of double-stranded target-epitope specific oligonucleotides, wherein the individual double-stranded target-epitope specific oligonucleotides are either covalently linked to a corresponding individual structurally distinct antibody, cleaved from the corresponding individual structurally distinct antibody, or contain a reverse complement of an oligonucleotide covalently linked to or cleaved from the corresponding individual structurally distinct antibody. In some cases, the target specific oligonucleotides contain: a) target-epitope specific barcode sequences, wherein the target-epitope specific barcode sequences are the same for any one structurally distinct antibody and different for all other structurally distinct antibodies; b) optional unique molecular identifier sequences, wherein the unique molecular identifier sequences are different for every target-epitope specific oligonucleotide; c) a partition-specific barcode sequence that is identical among all partition-specific oligonucleotides of any one mixture partition and different from all partition-specific barcode sequences in other mixture partitions of the plurality of mixture partitions; d) a first 5' region comprising a first sequencing primer binding region; and e) a second 5' region comprising a second sequencing primer binding region, wherein the first and second primer binding regions are on opposite strands of the double stranded target-epitope specific oligonucleotide, are structurally different from each other, and flank the target-epitope specific barcode sequence, partition-specific barcode sequence, and optional universal molecular identifier sequence.

The mixture partitions can be in discrete, physically separated, reaction chambers. For example, the mixture partitions can each be in separate wells off a micro-well or nano-well plate. As another example, the mixture partitions can be in emulsion droplets.

III. Methods

Described herein are methods for generating or using one or more of the foregoing compositions. The methods described herein include methods of synthesizing or providing barcoded oligonucleotides. The methods described herein further include methods of library generation. The methods described herein further include methods of cell fixation (cross-linking) and permeabilization, methods of partitioning, methods of sequencing, and methods of determining target biological component levels.

a. Methods of Cross-Linking and Permeabilizing Cells

Fixed cells can be fixed by contacting the cells with any suitable fixative. Such fixatives include, but are not limited to cross-linking agent such as, formaldehyde, paraformaldehyde (e.g., dissolved in water or a buffer), glutaraldehyde, a combination of formaldehyde and paraformaldehyde (e.g., dissolved in water or a buffer), a combination of glutaraldehyde and formaldehyde, glutaraldehyde and paraformaldehyde (e.g., dissolved in water or a buffer), or glutaraldehyde, formaldehyde and paraformaldehyde (e.g., dissolved in water or a buffer). Such fixatives can additionally or alternatively include agents that do not covalently cross-link, such as alcohol fixatives or denaturants that precipitate biological components (e.g., proteins) in situ. Generally, the fixation is performed in bulk prior to partitioning.

The fixed cells can be permeabilized by contacting the fixed cells with any suitable permeabilization reagent. Alternatively, cells can be fixed and permeabilized simultaneously by contacting the cells with a fixative and peremabilization agent, or contacting the cells with a composition that both fixes and permeabilizes the cells. Permeabilization reagents include, but are not limited to, non-ionic surfactants. A surfactant can be a detergent and/or a wetting agent. In some embodiments, the surfactant contains a hydrophilic and a hydrophobic portion and is therefore amphipathic. Exemplary non-ionic surfactants include, but are not limited to, block copolymers of polypropylene oxide and polyethylene oxide (e.g., poloxamers). Exemplary poloxamers include, but are not limited to, those sold under the trade names PLURONIC® and TETRONIC®, such as. Exemplary non-ionic surfactants further include polyethylene glycol derivative surfactants such as Triton® surfactants (e.g., Triton® X-100), polyoxyethylene derivatives of sorbitan monolaurate such as Tween® 20, those containing a polyethylene tail and an aromatic hydrocarbon head group such as Nonidet® P40, digitonin, and saponin.

Cells can be fixed and permeabilized, contacted with a library of binding elements conjugated to target ID barcoded oligonucleotides, washed to remove unbound and non-specifically bound binding elements, and partitioned.

b. Methods of Generating Barcoded Oligonucleotides and Libraries Containing Such Barcoded Oligonucleotides Barcodes, including target ID barcodes, UMI barcodes, partition-specific barcodes, sample index barcodes, and combinations thereof can be generated by solid phase synthesis methods as known in the art, including split and mix (also referred to as split and pool) synthesis schemes. In some cases, the solid phase synthesis scheme (e.g., split and mix synthesis scheme) is a reverse-amidite solid phase synthesis scheme (see, e.g., Macosko, et al., 2015, Cell 161, 1202-14). In some cases, one or more of the barcodes are generated by a combination of iterative single-nucleotide split and mix solid phase synthesis and solid-phase coupling of polynucleotide fragments containing multiple nucleotides (e.g., 2, 3, 4, 5, 6, 7, 8, or more) (see, e.g., H. C. Fan, et al., 2015, Science 347, 1258367 (2015). DOI 10.1126/science.1258367). In some cases, one or more barcodes are individually synthesized on separate oligonucleotide primers and oligonucleotides containing multiple combinations of such barcodes are generated by hybridization of the oligonucleotide primers to a template containing one or more other barcodes and extension of the hybridized primer with a polymerase. For example, an oligonucleotide containing a target ID barcode and optionally a UMI barcode can be hybridized to an oligonucleotide primer containing a partition-specific barcode, the primer can be extended by a polymerase to generate an oligonucleotide containing a target ID barcode, the optional UMI barcode, and the partition-specific barcode.

A plurality of such barcoded oligonucleotides can be synthesized to provide a library of barcoded oligonucleotides. In some cases, a library of target ID barcoded oligonucleotides that can further contain an optional UMI barcode is synthesized. Similarly, a library of partition-specific barcoded oligonucleotides can be synthesized, e.g., onto a plurality of solid surfaces (e.g., beads). In some cases, the library of target ID barcoded oligonucleotides is conjugated to a library of binding elements.

c. Methods of Partitioning

Described herein are methods of generating a plurality of mixture partitions containing any one or more of the compositions described herein. In one aspect, a method for generating a plurality of mixture partitions is provided herein, the method including: i) providing a plurality of fixed and permeabilized single cells, wherein the individual fixed and permeabilized single cells contain the target biological components of the cell, such as target proteins of the single cell; ii) incubating the fixed and permeabilized plurality of single cells with a library of at least about 10 structurally distinct binding elements (e.g., antibodies), where the binding elements are conjugated to target ID barcoded oligonucleotides, thereby binding the binding elements to their corresponding target biological components to form a plurality of binding element library—single-cell target biological component complexes. In some cases, the complexes are washed to remove unbound binding elements or remove non-specifically bound binding elements. The complexes can be partitioned into a plurality of mixture partitions.

In some cases, mixture partitions that do not contain a single cell and/or contain multiple cells can be removed or discarded. A plurality of partition-specific barcode oligonucleotides can also be partitioned into the plurality of partitions, and optionally mixture partitions that do not contain a single partition-specific barcode sequence and/or contain multiple partition-specific barcode sequences can be removed, disregarded, or discarded. In some cases, mixture partitions that do not contain a single partition-specific barcode sequence and/or contain multiple partition-specific barcode sequences can be identified by the absence of a bead or the presence of multiple beads respectively. Such absence or presence can detectably affect partition size, partition density, an optical property of the partition, and the like, allowing selection and separate handling of these partitions.

In some cases, the partitions can be subjected to a lysis condition to lyse the cells in the partitions, thereby forming a plurality of partitions having a barcoded hydrogel particle and nucleic acid from a single cell. In some cases, the partitions can be heated to lyse the cells and melt the hydrogel, thereby forming a plurality of partitions having sol/hydrogel and nucleic acid from a single cell.

In some cases, the method comprises performing iv) before v), and the partition-specific barcode oligonucleotides are partitioned into a plurality of mixture partitions comprising the antibody library—single-cell complexes. In some cases, the method comprises performing v) before iv), and the antibody library—single-cell complexes are partitioned into a plurality of mixture partitions comprising the partition-specific barcode oligonucleotides.

In some cases, the library of binding elements contains at least about 10, and no more than about 100,000, or at least about 10, and no more than about 10,000, structurally distinct antibodies conjugated to the target-epitope specific oligonucleotides. In some cases, the partition-specific barcode oligonucleotides are covalently linked to a bead with an optionally cleavable linker. In some cases, the partition-specific barcode oligonucleotides are cleaved from the bead and hybridized to the target ID barcoded oligonucleotides. In some cases, the target ID barcoded oligonucleotides are cleaved from the binding elements and hybridized to the partition-specific barcode oligonucleotides.

Partitions can include any of a number of types of partitions, including solid partitions (e.g., wells, reaction chambers, or tubes) and fluid partitions (e.g., aqueous droplets within an oil phase). In some embodiments, the partitions are droplets. In some embodiments, the partitions are micro channels. Methods and compositions for partitioning a sample are described, for example, in published patent applications WO 2010/036352, US 2010/0173394, US 2011/0092373, and US 2011/0092376, the entire content of each of which is incorporated by reference herein.

In some aspects, the number of partitions is chosen to ensure that a minority of, a substantial minority of, few, substantially no, or no partitions contain multiple single cells, contain multiple different partition-specific barcode sequences, or both. The number of partitions necessary to ensure adequate partitioning is dependent on a number of factors, including, but not limited to: (a) the number of fixed and permeabilized single cells; (b) the method of partitioning; (c) the number of partition-specific barcode sequences; (d) whether the partition-specific barcode oligonucleotides are immobilized on a solid surface or in solution during partitioning; and (e) the desired statistical significance. Partitioning of partition-specific barcoded oligonucleotides that are free in solution such that few partitions contain multiple different partition-specific barcode sequences generally requires partitioning under dilute conditions that generate a large number of "empty" partitions that do not contain any partition-specific barcode oligonucleotides. Thus, in some embodiments, it is preferred to partition beads containing partition-specific barcode oligonucleotides immobilized thereon. In general, the number of partitions is, or is at least about, 500; 1000; 10,000; or 20,000; 30,000; 50,000; 60,000; 70,000; 80,000; 90,000; 100,000; 150,000; 200,000; 250,000; 300,000; 500,000; $10^6$, $10^7$, or more.

In some embodiments, the partitions are substantially uniform in shape and/or size. For example, in some embodiments, the partitions are substantially uniform in average diameter. In some embodiments, the partitions have an average diameter of about 0.001 microns, about 0.005 microns, about 0.01 microns, about 0.05 microns, about 0.1 microns, about 0.5 microns, about 1 microns, about 5 microns, about 10 microns, about 20 microns, about 30 microns, about 40 microns, about 50 microns, about 60 microns, about 70 microns, about 80 microns, about 90 microns, about 100 microns, about 150 microns, about 200 microns, about 300 microns, about 400 microns, about 500 microns, about 600 microns, about 700 microns, about 800 microns, about 900 microns, or about 1000 microns. In some embodiments, the partitions have an average diameter of less than about 1000 microns, less than about 900 microns, less than about 800 microns, less than about 700 microns, less than about 600 microns, less than about 500 microns, less than about 400 microns, less than about 300 microns, less than about 200 microns, less than about 100 microns, less than about 50 microns, or less than about 25 microns.

In some embodiments, the partitions are substantially uniform in volume. For example, the standard deviation of partition volume can be less than about 1 picoliter, 5 picoliters, 10 picoliters, 100 picoliters, 1 nL, or less than about 10 nL. In some cases, the standard deviation of partition volume can be less than about 10-25% of the average partition volume. In some embodiments, the partitions have an average volume of about 0.001 nL, about 0.005 nL, about 0.01 nL, about 0.02 nL, about 0.03 nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, or about 50 nL.

In some embodiments, reagents such as fixed and permeabilized cells, buffers, enzymes (e.g., polymerases for amplification, barcoding, and/or sequencing), substrates, nucleotides, primers, salts, etc. are mixed together prior to partitioning, and then the sample is partitioned. In some cases, the reagents include a polymerase and the sample is partitioned shortly after mixing reagents together so that substantially all, or the majority, of polymerase activity occurs after partitioning. In other cases, the reagents are mixed at a temperature in which the polymerase proceeds slowly, or not at all, the sample is then partitioned, and the reaction temperature is adjusted to allow the polymerase reaction to proceed. For example, the reagents can be combined on ice, at less than 5° C., or at 0, 1, 2, 3, 4, 5, 6, 7, 8, 9, 10, 11, 12, 13, 14, 15, 16, 17, 18, 19, 20, 20-25, 25-30, or 30-35° C. or more. In general, one of skill in the art will know how to select a temperature at which one or more polymerase enzymes are not active. In some cases, a combination of temperature and time are utilized to avoid substantial polymerase activity prior to partitioning.

In some cases, reagents can be mixed using one or more hot start polymerases, such as a hot start DNA-dependent DNA polymerase. Thus, fixed and permeabilized cells, buffers, salts, nucleotides, labels, primers, enzymes, etc. can be mixed and then partitioned. Subsequently, the polymerization reaction, including multiple rounds of polymerization and/or amplification, can be initiated by heating the partition mixtures to activate the one or more hot-start polymerases.

Additionally, reagents can be mixed together without one or more reagents necessary to initiate an enzymatic reaction (e.g., polymerization and/or amplification). The mixture can then be partitioned into a set of first partition mixtures and then the one or more essential reagents can be provided by fusing the set of first partition mixtures with a set of second partition mixtures that provide the essential reagent. Alternatively, the essential reagent can be added to the first partition mixtures without forming second partition mixtures. For example, the essential reagent can diffuse into the set of first partition mixture water-in-oil droplets. As another example, the missing reagent can be directed to a set of micro channels which contain the set of first partition mixtures.

In some embodiments, reagents can be mixed together to form a reaction mixture, and partitioned. Subsequently, one or more additional reagents can be added to the partitions. For example, one or more reagents can be injected into the partitions. In some cases, an electric field can be applied to an interface between a partition and a fluid to disrupt the interface and allow at least a portion of the fluid to enter the partition. As another example, one or more reagents can be directed to partitions in micro or nanoliter size wells via microfluidic techniques. Methods, compositions, and devices for injection of reagents into a partition can include, but are not limited to, those described in WO/2010/0151776.

Reagents that can be added by fusing partitions, injection, microfluidics or other means include but are not limited to amplification reagents, detection reagents, sequencing reagents, ligation reagents, barcoding reagents, or combinations thereof. For example, DNA-dependent DNA polymerase (and, optionally, one or more primers) can be added into a partition to amplify a template nucleic acid in the partition (e.g., an oligonucleotide containing one or more barcodes). As yet another example, barcodes, primers, ligase, polymerase, or combinations thereof can be added into a partition to barcode nucleic acid in the partition. In some cases, the barcodes are attached to, or otherwise incorporated in or associated with, a solid or gel support, and the solid or gel support with the barcodes—and optionally other barcoding reagents, such as primers, polymerase, ligase, or a combination thereof—are added to one or more partitions by fusion, injection, microfluidics, or other means.

In some embodiments, a partition is a droplet comprising an emulsion composition, i.e., a mixture of immiscible fluids (e.g., water and oil). In some embodiments, a droplet is an aqueous droplet that is surrounded by an immiscible carrier fluid (e.g., oil). In some embodiments, a droplet is an oil droplet that is surrounded by an immiscible carrier fluid (e.g., an aqueous solution). In some embodiments, the droplets described herein are relatively stable and have minimal coalescence between two or more droplets. In some embodiments, less than 0.0001%, 0.0005%, 0.001%, 0.005%, 0.01%, 0.05%, 0.1%, 0.5%, 1%, 2%, 3%, 4%, 5%, 6%, 7%, 8%, 9%, or 10% of droplets generated from a sample coalesce with other droplets. The emulsions can also have limited flocculation, a process by which the dispersed phase comes out of suspension in flakes. In some embodiments, the droplet is formed by flowing an oil phase through an aqueous sample comprising one or more of the compositions described herein.

The oil phase can comprise a fluorinated base oil which can additionally be stabilized by combination with a fluorinated surfactant such as a perfluorinated polyether. In some embodiments, the base oil comprises one or more of a HFE 7500, FC-40, FC-43, FC-70, or another common fluorinated oil. In some embodiments, the oil phase comprises an anionic fluorosurfactant. In some embodiments, the anionic fluorosurfactant is Ammonium Krytox (Krytox-AS), the ammonium salt of Krytox FSH, or a morpholino derivative of Krytox FSH. Krytox-AS can be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of Krytox-AS is about 1.8%. In some embodiments, the concentration of Krytox-AS is about 1.62%. Morpholino derivative of Krytox FSH can be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of morpholino derivative of Krytox FSH is about 1.8%. In some embodiments, the concentration of morpholino derivative of Krytox FSH is about 1.62%.

In some embodiments, the oil phase further comprises an additive for tuning the oil properties, such as vapor pressure, viscosity, or surface tension. Non-limiting examples include perfluorooctanol and 1H,1H,2H,2H-Perfluorodecanol. In some embodiments, 1H,1H,2H,2H-Perfluorodecanol is added to a concentration of about 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.25%, 1.50%, 1.75%, 2.0%, 2.25%, 2.5%, 2.75%, or 3.0% (w/w). In some embodiments, 1H,1H, 2H,2H-Perfluorodecanol is added to a concentration of about 0.18% (w/w).

In some embodiments, the emulsion is formulated to produce highly monodisperse droplets having a liquid-like interfacial film that can be converted by heating into microcapsules having a solid-like interfacial film; such microcapsules can behave as bioreactors able to retain their contents through an incubation period. The conversion to microcapsule form can occur upon heating. For example, such conversion can occur at a temperature of greater than about 40°, 50°, 60°, 70°, 80°, 90°, or 95° C. During the heating process, a fluid or mineral oil overlay can be used to prevent evaporation. Excess continuous phase oil can be removed prior to heating, or left in place. The microcapsules can be resistant to coalescence and/or flocculation across a wide range of thermal and mechanical processing.

Following conversion of droplets into microcapsules, the microcapsules can be stored at about −70°, −20°, 0°, 3°, 4°, 5°, 6°, 7°, 8°, 9°, 10°, 15°, 20°, 25°, 30°, 35° or, 40° C. In some embodiments, these capsules are useful for storage or transport of partition mixtures. For example, samples can be collected at one location, partitioned into droplets containing enzymes, buffers, and/or primers or other probes, optionally one or more polymerization reactions can be performed, the partitions can then be heated to perform microencapsulation, and the microcapsules can be stored or transported for further analysis.

The microcapsule partitions can resist coalescence, particularly at high temperatures. Accordingly, the capsules can be incubated at a very high density (e.g., number of partitions per unit volume). In some embodiments, greater than 100,000, 500,000, 1,000,000, 1,500,000, 2,000,000, 2,500,000, 5,000,000, or 10,000,000 partitions can be incubated per mL. In some embodiments, the incubations occur in a single well, e.g., a well of a microtiter plate, without inter-mixing between partitions. The microcapsules can also contain other components necessary for a reaction to occur during the incubation.

In some embodiments, a sample containing one or more of the compositions described herein is partitioned into at least 500 partitions, at least 1000 partitions, at least 2000 partitions, at least 3000 partitions, at least 4000 partitions, at least 5000 partitions, at least 6000 partitions, at least 7000 partitions, at least 8000 partitions, at least 10,000 partitions, at least 15,000 partitions, at least 20,000 partitions, at least 30,000 partitions, at least 40,000 partitions, at least 50,000 partitions, at least 60,000 partitions, at least 70,000 partitions, at least 80,000 partitions, at least 90,000 partitions, at least 100,000 partitions, at least 200,000 partitions, at least 300,000 partitions, at least 400,000 partitions, at least 500,000 partitions, at least 600,000 partitions, at least 700,000 partitions, at least 800,000 partitions, at least 900,000 partitions, at least 1,000,000 partitions, at least 2,000,000 partitions, at least 3,000,000 partitions, at least 4,000,000 partitions, at least 5,000,000 partitions, at least 10,000,000 partitions, at least 20,000,000 partitions, at least 30,000,000 partitions, at least 40,000,000 partitions, at least 50,000,000 partitions, at least 60,000,000 partitions, at least 70,000,000 partitions, at least 80,000,000 partitions, at least 90,000,000 partitions, at least 100,000,000 partitions, at least 150,000,000 partitions, or at least 200,000,000 partitions.

In some embodiments, a sample containing fixed and permeabilized cells and one or more of the compositions described herein is partitioned into a sufficient number of partitions such that all, substantially all, or at least a majority of partitions have no more than 1 fixed and permeabilized cell. In some embodiments, the sample is partitioned into a sufficient number of partitions such that all, substantially all, or at least a majority of partitions have no more than 1 partition-specific barcode sequence.

In some embodiments, emulsion droplet partitions that are generated are substantially uniform in shape and/or size. For example, in some embodiments, the droplets are substantially uniform in average diameter. In some embodiments, the droplets that are generated have an average diameter of about 0.001 microns, about 0.005 microns, about 0.01 microns, about 0.05 microns, about 0.1 microns, about 0.5 microns, about 1 microns, about 5 microns, about 10 microns, about 20 microns, about 30 microns, about 40 microns, about 50 microns, about 60 microns, about 70 microns, about 80 microns, about 90 microns, about 100 microns, about 150 microns, about 200 microns, about 300 microns, about 400 microns, about 500 microns, about 600 microns, about 700 microns, about 800 microns, about 900 microns, or about 1000 microns. In some embodiments, the droplets that are generated have an average diameter of less than about 1000 microns, less than about 900 microns, less than about 800 microns, less than about 700 microns, less than about 600 microns, less than about 500 microns, less than about 400 microns, less than about 300 microns, less than about 200 microns, less than about 100 microns, less than about 50 microns, or less than about 25 microns. In some embodiments, the droplets that are generated are non-uniform in shape and/or size.

In some embodiments, the emulsion droplet partitions that are generated are substantially uniform in volume. For example, the standard deviation of droplet volume can be less than about 1 picoliter, 5 picoliters, 10 picoliters, 100 picoliters, 1 nL, or less than about 10 nL. In some cases, the standard deviation of droplet volume can be less than about 10-25% of the average droplet volume. In some embodiments, the droplets that are generated have an average volume of about 0.001 nL, about 0.005 nL, about 0.01 nL, about 0.02 nL, about 0.03 nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, or about 50 nL.

d. Methods of Performing Single-Cell Resolution Analysis of Target Biological Component Levels Described herein is a method for performing single-cell resolution target biological component analysis by high throughput sequencing, the method comprising: i) forming or providing a plurality of one or more of the foregoing mixture partitions, wherein the mixture partitions further comprise a thermostable polymerase, and a) the target biological component specific oligonucleotides are covalently conjugated to the structurally distinct binding elements with a cleavable linker; b) the partition-specific oligonucleotides are covalently conjugated to the beads with a cleavable linker; or c) a) and b); and ii) cleaving the cleavable linkers.

In some embodiments, the method further includes: c; iii) firstly hybridizing: a) the 3' priming regions of the partition-specific oligonucleotides to 5' ends of the target biological component specific oligonucleotides, and extending the hybridized partition specific oligonucleotides with the polymerase, thereby generating double stranded target biological component specific oligonucleotides comprising the target biological component specific barcode sequences, the partition-specific barcode sequences, and optionally universal molecular identifier sequences; or b) the 3' priming regions of the universal primers to 5' ends of the target biological component specific oligonucleotides, and extending the hybridized universal primers with the polymerase, thereby generating double stranded target biological component specific oligonucleotides comprising a universal priming region, the target biological component specific barcode sequences, and optionally universal molecular identifier sequences.

In some embodiments, the method further includes: iv) secondly hybridizing: a) the 3' priming regions of the partition-specific oligonucleotides to 5' ends of the double-stranded target biological component specific oligonucleotides comprising the universal priming regions, if present, and extending the hybridized partition specific oligonucleotides with the polymerase; or b) the 3' priming regions of the universal primers to 5' ends of the double-stranded target biological component specific oligonucleotides comprising the partition-specific barcode sequences, if present, and extending the hybridized universal primers with the polymerase, thereby generating double stranded target biological component specific oligonucleotides comprising the universal priming region, the target biological component specific barcode sequences, the partition-specific barcode sequences, and optionally universal molecular identifier sequences.

In some embodiments, the method further comprises amplifying the (e.g., double-stranded) target biological component oligonucleotides of iv). In some embodiments, the method further comprises combining and sequencing the amplified double-stranded target biological component specific oligonucleotides in a high-throughput sequencing reaction to obtain a number of target biological component specific oligonucleotide sequence reads, wherein the sequencing comprises: a) determining the partition-specific barcode sequence, thereby determining the single cell to which the sequencing data corresponds; and b) determining the target biological component barcode sequence, thereby determining the biological component to which the sequencing data corresponds. Generally, the number of target biological component specific oligonucleotide sequence reads, in which the reads have the same partition-specific barcode sequence and target biological component specific barcode sequence is proportional to a level of the biological component in the single cell to which the sequencing data corresponds.

In some embodiments, the double stranded target biological component specific oligonucleotides further comprise the universal molecular identifier sequences, and the method further comprises determining the universal molecular identifier sequence; and, normalizing the number of target biological component specific oligonucleotide sequence reads for amplification bias by identifying stranded target biological component specific oligonucleotide sequences having the same universal molecular identifier sequence as amplification duplicates. In some cases, the double stranded target biological component specific oligonucleotides further comprise a sample index sequence, and the method further comprises determining the sample index sequence; and, identifying the source of the single cell to which the sequencing data corresponds.

In some embodiments, a method described herein includes one or more, or all, of the following with reference to FIG. 1: a population of, e.g., at least, 10's to 10,000 cells (1) are fixed and permeabilized (2), and contacted with a library of such antibody-oligonucleotide conjugates to form antibody:ligand complexes, and unbound antibodies are washed away (3). The single cells are partitioned into a plurality of droplets, to form a plurality of droplets that each contain a single cell, a polymerase, a universal primer and a bead, where the bead is conjugated to a plurality of oligonucleotides having a droplet-specific barcode and a primer region (4). The oligonucleotides conjugated to the beads and/or the oligonucleotides conjugated to the antibodies are cleaved. The antibody oligonucleotides are amplified with the polymerase universal primer and bead oligonucleotides, converting target protein levels into countable sequence tags (5). The droplets are combined to generate a sequencing library (6), which is sequenced using next generation (high-throughput) sequencing methodologies, converting sequence tag counts to target protein levels (7).

Although the foregoing invention has been described in some detail by way of illustration and example for purposes of clarity of understanding, one of skill in the art will appreciate that certain changes and modifications may be practiced within the scope of the appended claims. All patents, patent applications, and other publications, including GenBank Accession Numbers, cited in this application are incorporated by reference in the entirety for all purposes.

What is claimed is:

1. A method for generating a plurality of mixture partitions, the method comprising:
   (i) providing a plurality of fixed and permeabilized single cells;
   (ii) incubating the plurality of single cells with a library of at least 10 structurally distinct antibodies that have a specific binding affinity for target epitopes of cellular proteins, wherein each of the at least 10 antibodies is conjugated to a different epitope-specific oligonucleotide comprising a barcode sequence that identifies the target epitope, a unique molecular identifier (UMI), a first primer binding sequence, and a second primer binding sequence, wherein the incubating results in binding of the antibodies to their corresponding epitopes, if present, to form antibody-epitope complexes;
   (iii) washing away unbound antibodies;
   (iv) partitioning, after the incubating and washing steps, the plurality of fixed and permeabilized single cells into a plurality of mixture partitions; and
   (v) providing a plurality of partition-specific oligonucleotides to each mixture partition, wherein each partition-specific oligonucleotide comprises a different barcode sequence and a primer binding sequence that is complementary to the first primer binding sequence of the epitope-specific oligonucleotides,
   wherein each partition-specific oligonucleotide is covalently linked to a bead.

2. The method of claim 1, wherein the method comprises incubating the plurality of single cells with the library of at least 10, and no more than about 10,000, structurally distinct antibodies conjugated to the epitope-specific oligonucleotides.

3. The method of claim 1, wherein the method comprises performing (iv) before (v), and the partition-specific oligonucleotides are partitioned into a plurality of mixture partitions comprising the antibody-epitope complexes.

4. The method of claim 1, wherein the method comprises performing (v) before (iv), and the antibody-epitope complexes are partitioned into a plurality of mixture partitions comprising the partition-specific oligonucleotides.

5. The method of claim 1, wherein step (iv) comprises discarding mixture partitions that do not contain a single cell and/or contain multiple cells.

6. The method of claim 1, wherein step (v) comprises discarding mixture partitions that do not contain a single partition-specific oligonucleotide and/or contain multiple partition-specific oligonucleotides.

7. The method of claim 1, wherein the partition-specific oligonucleotides are covalently linked to a bead with a cleavable linker.

8. The method of claim 1, wherein the cells are lysed.

9. The method of claim 1, wherein the plurality of mixture partitions comprise a primer that binds to the second primer binding sequence.

* * * * *